US009468559B2

(12) United States Patent  
Rathjen

(10) Patent No.: US 9,468,559 B2  
(45) Date of Patent: *Oct. 18, 2016

(54) OPHTHALMOLOGICAL APPARATUS FOR THE BREAKDOWN OF EYE TISSUE

(71) Applicant: SIE AG Surgical Instrument Engineering, Port (CH)

(72) Inventor: Christian Rathjen, Bremen (DE)

(73) Assignee: SIE AG SURGICAL INSTRUMENT ENGINEERING (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/550,756

(22) Filed: Nov. 21, 2014

(65) Prior Publication Data

US 2015/0073397 A1   Mar. 12, 2015

Related U.S. Application Data

(63) Continuation of application No. 10/858,064, filed on Jun. 2, 2004, now Pat. No. 8,920,408.

(30) Foreign Application Priority Data

Jun. 10, 2003 (EP) .................................. 03405415

(51) Int. Cl.  
 A61F 9/009 (2006.01)  
 A61F 9/008 (2006.01)  
 A61B 17/30 (2006.01)

(52) U.S. Cl.  
CPC ............. *A61F 9/009* (2013.01); *A61F 9/0084* (2013.01); *A61F 9/00827* (2013.01); *A61F 9/00836* (2013.01); *A61B 2017/306* (2013.01); *A61F 2009/00853* (2013.01); *A61F 2009/00872* (2013.01); *A61F 2009/00897* (2013.01)

(58) Field of Classification Search  
CPC ............... A61F 9/008; A61F 9/00802; A61F 9/00804; A61F 9/00821; A61F 9/00825; A61F 9/00872  
USPC ................. 606/4–6, 10–12, 166; 607/88–92; 128/898  
See application file for complete search history.

(56) References Cited

U.S. PATENT DOCUMENTS 4,477,159 A * 10/1984 Mizuno et al. ............... 351/221  
4,665,913 A *  5/1987 L'Esperance, Jr. ............... 606/3

(Continued)

FOREIGN PATENT DOCUMENTS

DE   198 31 674 A1   1/2000  
WO   WO 89/06519      7/1989  
WO   WO 99/65431    12/1999

*Primary Examiner* — Ahmed Farah  
(74) *Attorney, Agent, or Firm* — Ostrolenk Faber LLP

(57) ABSTRACT

An ophthalmological apparatus includes a handle for manually holding and applying the ophthalmological apparatus, fastening abilities for fixing the ophthalmological apparatus at an eye, a light source, and a light projector for the focused projection of light pulses for punctiform tissue breakdown at a focal point in the interior of the eye tissue. The ophthalmological apparatus also includes a movement driver for moving the light projector. The movement of the light projector and therefore that of the focal point with the assistance of the movement driver permits a dimensioning of the optical projection system of the light projector which is substantially smaller than in the case of an ophthalmological apparatus where the focal point is moved exclusively by an optical projection system.

24 Claims, 8 Drawing Sheets

(56) References Cited

U.S. PATENT DOCUMENTS

| | | | |
|---|---|---|---|
| 4,901,718 A | 2/1990 | Bille et al. ........................... 60/4 |
| 5,549,632 A | 8/1996 | Lai ..................................... 606/5 |
| 6,146,375 A * | 11/2000 | Juhasz et al. ...................... 606/6 |
| 6,494,878 B1 | 12/2002 | Pawlowski et al. .............. 606/4 |
| 7,018,376 B2 | 3/2006 | Webb et al. ....................... 606/4 |
| 7,351,241 B2 * | 4/2008 | Bendett ............... A61F 9/00827 128/898 |
| 8,920,408 B2 * | 12/2014 | Rathjen ............................. 606/5 |

\* cited by examiner

OPHTHALMOLOGICAL APPARATUS FOR THE BREAKDOWN OF EYE TISSUE

CROSS-REFERENCE TO RELATED APPLICATIONS

This application is a continuation of U.S. patent application Ser. No. 10/858,064, filed Jun. 2, 2004, which claims the benefit of European Patent Application No. 03 405 415.5, filed Jun. 10, 2003, the contents of which are incorporated herein by reference.

TECHNICAL FIELD

The present invention relates to an ophthalmological apparatus for the breakdown of eye tissue. The invention relates, in particular, to an ophthalmological apparatus which comprises a handle for manually holding and applying the ophthalmological apparatus, which comprises fastening means for fixing the ophthalmological apparatus at an eye, and which comprises a light source and a light projector, optically connected to the light source, for the focussed projection of light pulses for punctiform tissue breakdown at a focal point in the interior of the eye tissue.

PRIOR ART

Instances of ametropia such as myopia (short-sightedness), hyperopia (longsightedness or far-sightedness) or astigmatism can nowadays be permanently corrected by refractive surgical treatment. Refractive surgical treatments are surgical operations on the eye which change the optical refractive power of the eye with the aim of bringing it as close to a desired value as close as possible. One of the most important methods in refractive surgery is so-called laser-assisted in situ keratomileusis (LASIK) in which the interior of the cornea is removed with the aid of a computer controlled eximer laser after a corneal flap has previously been partially severed and folded away. In order to produce the corneal flap, use is made of mechanical microkeratomes in which a driven scalpel cuts the corneal flap. Recently, such corneal flaps can also be cut with the aid of strongly focussed femtosecond laser pulses, which have pulse widths of typically 100 fs to 1000 fs (1 fs=$10^{-15}$ s). The risks existing during use of a mechanically oscillating scalpel are avoided by the use of a femtosecond laser. Such a system is marketed by IntraLase Corp. in Irvine, Calif., USA under the name of Pulsion FS Laser. The overall size of the known systems having femtosecond lasers is comparable to the overall size of an eximer laser, its advantage being that the space required for the eximer laser is required once again in the treatment room for the femtosecond laser system. In addition, after the cutting of the corneal flap by the femtosecond laser system, the patient must be transferred to the eximer laser. The overall size of the femtosecond laser is determined, inter alia, by the light source used, the scanner technology and the attendant beam guidance systems. The laser beam is focussed inside a large stationary lens system by means of beam-deflecting optical elements onto the tissue areas of the eye to be separated. For design reasons, the maximum achievable numerical aperture (NA, proportional to half the sine of the aperture angle of the objective) of the focussing optical system is limited in this case (typically NA=0.2-0.3). For a given work area, for example the entire cornea, the scanning optics (typically an f-Theta optic) requires a minimum working distance. In conjunction with the required movement and the achievable size of the beam-deflecting optical elements, the working distance determines a design limit for the diameter of the scanning optics. A further upper design limit for the diameter follows from instances of shadings or collisions with body parts (eyebrows, nose). Even in the case of large diameters, it is always possible to eliminate only a subarea of the optics with a scanning laser beam. The result of this is an upper design limit for the effective useful numerical aperture of the optics. High apertures are desirable because with high NA it is possible to produce small focal points, and thus a smaller cutting zone per pulse. Less gas is produced per pulse in smaller cutting zones than in large cutting zones. More precise cuts can be made by means of smaller gas bubbles since, inter alia, the cutting zones are not deformed by the internal gas pressure. In addition, high NA require disproportionately less energy per pulse to make a cut. With a lower energy, there is also a reduction in the cavitation bubbles produced by the laser pulse, and this additionally has a positive effect on the cutting quality. Furthermore, the retina is subject to less stress from the more strongly diverging beams downstream of the focal point given high NA. A further advantage is that for high NA local contaminants in the vicinity of the corneal surface have less effect in reducing the intensity at the focus.

Patent specification U.S. Pat. No. 5,549,632 describes an ophthalmological apparatus having a laser source for the breakdown of eye tissue, which can be used inter alia for cutting corneal flaps. The apparatus in accordance with U.S. Pat. No. 5,549,632 comprises a laser source and a projection head, optically connected to the laser source, in a housing separate from the laser source. The apparatus in accordance with U.S. Pat. No. 5,549,632 also comprises beam control means which control the beam path of the laser pulses emitted by the laser source such that points in a reference frame fixed relative to the laser source are imaged via an optical connection onto corresponding points in a reference frame fixed in relation to the projection head. The optical connection has to be designed in a complicated fashion as an articulated mirror arm so that the light pulses deflected by the beam control means can be imaged relative to the reference frame of the hand-held appliance. The connection of the projection head to an applanation plate which can be permanently connected to the eye means that the fixed reference frame of the projection head in accordance with U.S. Pat. No. 5,549,632 is permanently imaged onto the applanation plate and thus onto the eye. In accordance with U.S. Pat. No. 5,549,632, the laser pulses are led to the desired positions of the eye by using the beam control means to control the position of the pulsed laser beam relative to the applanation plate, and to image it onto the eye via the optical connection and the optical projection system of the projection head. For example, in order to carry out cuts of 5 to 15 mm in length, the optical projection system of the projection head must have optical lenses whose diameter is greater than the diameter of the eyeball. A projection head of such large dimension will cover the view onto the eye to be treated. Furthermore, the numerical aperture of the apparatus in accordance with U.S. Pat. No. 5,549,632 is small, as may be seen from the relatively small convergence of the beams.

A further ophthalmological apparatus for focussing laser pulses onto the eye is described in U.S. Pat. No. 4,901,718. In accordance with U.S. Pat. No. 4,901,718 it is possible for the position of the laser optics to be varied relative to the eye. The apparatus in accordance with U.S. Pat. No. 4,901,718 also achieves only a small numerical aperture, this being due to the choice of the scanning method and the beam guidance. As in the apparatus according to U.S. Pat. No.

5,549,632, the outlay on equipment for beam guidance is also considerable in the apparatus in accordance with U.S. Pat. No. 4,901,718.

Large lens systems also have the disadvantage of causing apparatuses to become heavy and unwieldy, thus complicating manual holding and application.

SUMMARY OF THE INVENTION

It is an object of the present invention to propose a new ophthalmological apparatus for the breakdown of eye tissue, which does not have at least certain disadvantages of the prior art, and which is suitable, in particular, for punctiform tissue breakdown in the interior of the eye tissue.

In accordance with the present invention, these objects are achieved, in particular, by the elements of the independent claims. Further advantageous embodiments also follow from the dependent claims and the description.

The above-named objects are achieved by the present invention by virtue of the fact that, in particular, a movement driver for moving the light projector is provided for an ophthalmological apparatus which comprises a handle for manually holding and applying the ophthalmological apparatus, fastening means for fixing the ophthalmological apparatus at an eye, for example by low pressure, and a light source and a light projector, optically connected to the light source, for the focussed projection of light pulses for punctiform tissue breakdown at a focal point in the interior of the eye tissue. Through the mechanical movement of the light projector, the movement driver advantageously permits the focal point of the punctiform tissue breakdown to move automatically to a number of points in the interior of the eye tissue. Because the focal point is moved with the assistance of the movement driver, it is possible in conjunction with the same action range of the ophthalmological apparatus for the optical projection system of the light projector to be of substantially smaller dimension than in the case of an ophthalmological apparatus in which the focal point is moved exclusively by the optical projection system. In addition, owing to such miniaturization of the optical projection system, it is possible to achieve a sharper focussing of the light pulses, that is to say a sharper imaging of the light pulses at the focal point in the interior of the eye tissue, since when the ophthalmological apparatus is applied to the eye the distance between the optical projection system and the eye is reduced, and a smaller working distance results than in the case of systems in which the focal point is moved in an exclusively optical fashion, and a higher NA thereby results in conjunction with smaller dimensions. The sharper focussing of the light pulses permits more precise treatments with smoother cut surfaces and less stress for the eye.

The movement driver and the light projector are preferably set up and coupled such that the light projector can be moved into a position in which at least a portion of the eye can be examined in top view upon fixing the ophthalmological apparatus at the eye. This enables the user to fix the ophthalmological apparatus at the eye to be treated given an unimpeded view of this eye.

The movement driver and the light projector are preferably set up and coupled such that the light projector can be moved equidistantly from a movement surface. As a result, the focal point for the punctiform tissue breakdown can be moved by the movement driver such that cuts and cut surfaces are produced equidistantly from the movement surface in the interior of the eye tissue.

The movement driver and the light projector are advantageously set up and coupled such that the light projector can be moved equidistantly from a flat movement surface. As a result, the focal point for the punctiform tissue breakdown can be moved by the movement driver such that cuts and flat cut surfaces are produced equidistantly from a movement plane in the interior of the eye tissue.

In a variant design, the movement driver is set up to move the light projector along a translation line equidistant from the movement surface. Particularly in the case of a flat movement surface, it is thereby possible to use a simple mechanical displacement of the light projector along an equidistant translation axis to produce straight cuts in the interior of the eye tissue. In a variant design, the ophthalmological apparatus comprises a second such movement driver which is set up to move the light projector along a second translation line equidistant from the movement surface. By the combination of two translatory movement drivers, it is thereby possible to use a simple mechanical displacement of the light projector along two translation lines to produce cut surfaces in the interior of the eye tissue, which surfaces are equidistant from the movement surface; flat cut surfaces can thus be produced in the case of the flat movement surface.

In a variant design, the movement driver is set up to move the light projector about an axis of rotation normal to the movement surface. Consequently, the focal point for the punctiform tissue breakdown can be moved by the movement driver such that circular cuts equidistant from the (flat) movement surface are produced in the interior of the eye tissue.

In a variant design, the movement driver is set up to move the light projector along a translation line equidistant from the movement surface, and the ophthalmological apparatus comprises a further movement driver, which is set up to move the light projector about an axis of rotation normal to the movement surface. Particularly in the case of a flat movement surface, the combination of displacement and rotation of the light projector can thus produce flat cut surfaces in the interior of the eye tissue in a way similar to milling.

The ophthalmological apparatus is preferably set up to control the spacing between the focal point and the movement surface. By varying the spacing between the focal point and the movement surface, it is possible to move the focal point for the punctiform tissue breakdown so as to produce in the interior of the eye tissue cuts and cut surfaces which are not equidistant from the movement surface and are, for example, perpendicular to the movement surface.

In a variant design, the ophthalmological apparatus is set up to control the position of the focal point along the axis of projection of the light pulses. By varying the position of the focal point along the axis of projection of the light pulses, the spacing between the focal point and the movement surface can be varied, as a result of which, as described above, there are produced in the interior of the eye tissue cuts and cut surfaces which are not equidistant from the movement surface and are, for example, perpendicular to the movement surface.

In a variant design, the light projector comprises light-deflecting optical elements for the focussed projection of the light pulses along a scanning line. By using light-deflecting optical elements, typically movable light-deflecting optical elements, the focal point can be moved optically such that tissue is broken down in the interior of the eye tissue in a punctiform fashion along the scanning line. By combining this optical movement of the focal point with the above-described translatory or rotatory mechanical movements of the light projector, it is possible, in turn, for there to be produced in the interior of the eye tissue cut surfaces equidistant from the movement surface, or from the movement plane.

The ophthalmological apparatus preferably comprises a contact body which can be mounted onto the eye and is transparent at least at some points and is designed and arranged such that it places equidistantly from the movement surface an area of the eye which is contacted in the mounted state. Since the focal point for the punctiform tissue breakdown in the interior of the eye tissue is moved in a fashion equidistant from the movement surface, the contact body renders it possible in a simple way for there to be produced in the interior of the eye tissue cuts and cut surfaces equidistant from the contacted area of the eye. If the focal point is moved in a fashion equidistant from the movement surface, use is preferably made of a contact body designed as an applanation body which is arranged such that in the mounted state it applanates the contacted area of the eye parallel to the movement surface. If the focal point is moved in a fashion equidistant from a concave or convex movement surface, use if preferably made of a contact body designed as a contour body which is designed and arranged such that in the mounted state it forms the contacted area of the eye parallel to the concave or convex movement surface.

In a variant design, the contact body is permanently connected to the fastening means such that it is fixed at the eye to be treated.

In a variant design, the contact body is permanently connected to the light projector. This produces a permanent reference from the light projector to the contact body, the contact body being moved together with the light projector in the event of movement, preferably of translation.

In a variant design, the ophthalmological apparatus comprises a holding apparatus for removably holding the contact body. Consequently, disposable contact bodies can be used to preserve hygiene and to avoid infections. This advantage is achieved, in particular, when the contact body is permanently connected to the fastening means, and both the contact body and the fastening means can be connected to the ophthalmological apparatus in a fashion capable of removal via the holding apparatus, and can be disposed or sterilized after use on a patient.

In a variant design, the light source comprises a femtosecond laser. A femtosecond laser comprises a laser generator for producing laser pulses with pulse widths of from 1 fs to 1 ps (1 fs=$10^{-15}$ s). Laser pulses with such pulse widths permit the targeted punctiform breakdown of tissue in the interior of the eye tissue, mechanical and thermal side effects being strongly reduced in the surrounding tissue, such as are known from longer pulse widths.

In a variant design, the light source comprises a femtosecond laser which is designed as a fibre laser. A femtosecond fibre laser can be wound up in a space-saving fashion such that the ophthalmological apparatus can be designed as an inherently closed unit which comprises the light source and the light projector optically connected to the light source, and which can be applied manually and can be fixed at the eye.

In a variant design, the light source comprises an optical oscillator, and the optical oscillator is connected to the light projector via an optical expander, via an optical transport line and via an optical compressor, the optical transport line comprising an optical amplifier. The optical expander extends a short femtosecond laser pulse produced by means of the optical oscillator, for example by the factor $10^4$. The extended laser pulse is of low intensity, and can be amplified to a greater amplitude by the optical amplifier. The optical compressor compresses the amplified, extended laser pulse and thereby the intensity of the laser pulse to a multiple of the peak value for which the optical amplifier is designed, for example by a factor of $10^4$. Laser pulses of great intensity can thus be produced with the aid of an optical amplifier of small dimension.

In a variant design, the optical transport line is designed as a photonic crystal. The design of the optical transport line as a photonic crystal, a so-called photonic crystal fibre, permits the transmission characteristics to be substantially improved by comparison with the conventional fibre lines, such that high powers can be transmitted and that the laser pulses are not "washed out" by dispersion.

In a variant design, the ophthalmological apparatus comprises carrying means for fastening the ophthalmological apparatus movably on an object external to the ophthalmological apparatus, for example on an eximer laser. Such carrying means permit the weight of the ophthalmological apparatus to be transferred to the external object, and permits the eye to be treated to be relieved.

In a variant design, the ophthalmological apparatus is set up to move the focal point such that the tissue breakdown in the interior of the eye tissue separates from the remaining eye tissue a tissue flap which remains connected to the eye in a residual area.

In a variant design, the ophthalmological apparatus comprises control means for controlling the position of the focal point in such a way that the tissue breakdown in the interior of the eye tissue separates from the remaining eye tissue a tissue piece which remains connected to the eye in a residual area, the tissue flap having lateral surfaces which are produced by varying the spacing of the focal point from the movement surface.

BRIEF DESCRIPTION OF THE DRAWINGS

A design of the present invention is described below with the aid of an example. The example of the design is illustrated by the following attached figures:

FIG. 9b shows a further cross section of the tissue flap illustrated in FIG. 9a.

WAYS OF IMPLEMENTING THE INVENTION

Figure 1:
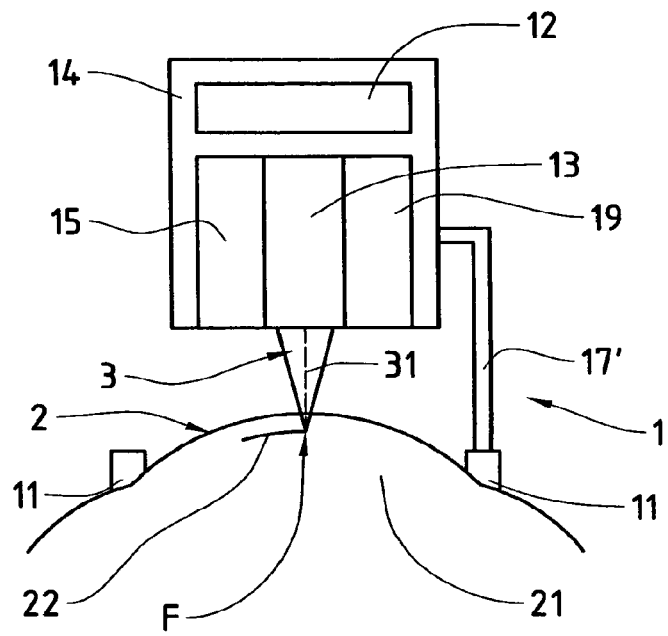
FIG. 1 shows a block diagram which schematically illustrates an ophthalmological apparatus which comprises a handle, fastening means, a light source, a light projector optically connected to the light source, and a movement driver for moving the light projector.

Mutually corresponding components are denoted in FIGS. 1 to 8 by identical reference symbols.

In FIGS. 1, 2, 3, 4a to 4f, 5a to 5c, 6a, 9a, 9b, 10a and 10b, the reference numeral 2 denotes an eye, in particular a human eye.

In FIGS. 1, 2, 3, 5a to 5c, 6a, 9a, 9b, 10a and 10b, the reference numeral 21 denotes eye tissue, in particular corneal tissue.

In FIGS. 1, 2, 3, 5a to 5c, 6a, 7 and 8, the reference numeral 1 denotes an ophthalmological apparatus which comprises a handle 14 for manually holding and applying the ophthalmological apparatus 1. As illustrated schematically in FIGS. 7 and 8, the handle 14 of the ophthalmological apparatus 1 can be designed in a projecting fashion. The ophthalmological apparatus 1 can, however, also be configured as a hand-held appliance such that its external form serves as a handle 14.

In FIGS. 1, 2, 3, 6a, 7 and 8, the reference numeral denotes fastening means 11 for fixing the ophthalmological apparatus 1 at the eye 2. The fastening means 11 comprise, for example, a suction ring or a number of suction elements which fix the ophthalmological apparatus 1 at the eye 2 by low pressure.

The ophthalmological apparatus 1 comprises a light projector 13 for the focussed projection of light pulses 3 for punctiform tissue breakdown at a focal point F in the interior of the eye tissue 21. The light projector 13 is optically connected to a light source 12. The light source 12 comprises a femtosecond laser, that is to say a laser generator for generating laser pulses with pulse widths in the femtosecond range of from 1 fs to 1 ps (1 fs=$10^{-15}$ s). The light source 12 comprises, for example, a femtosecond laser which is designed as a fibre laser (femtosecond fibre laser).

Figure 2:
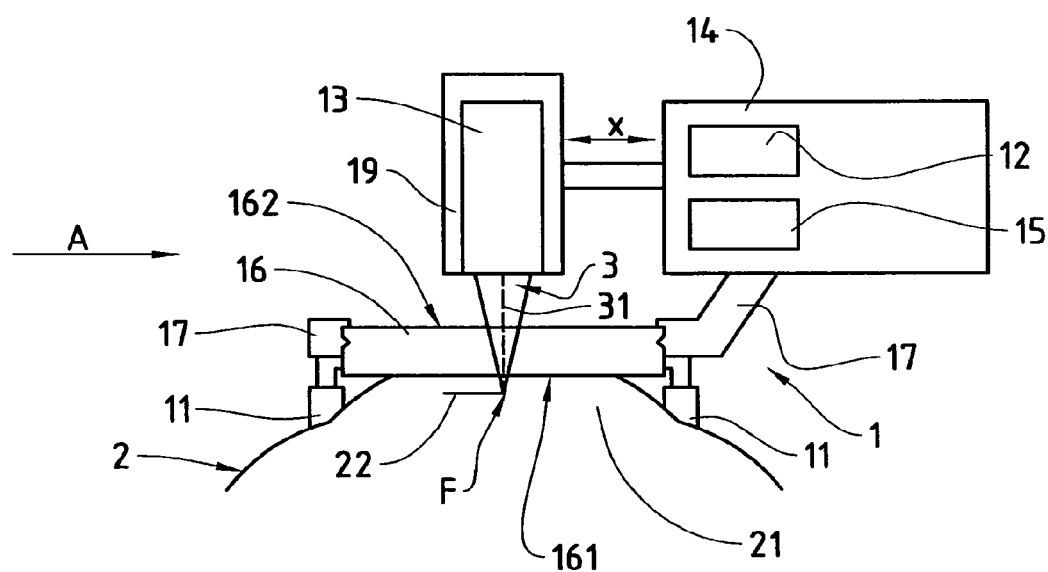
FIG. 2 shows a block diagram which schematically illustrates a design of the ophthalmological apparatus having a contact body which can be mounted on the eye and is transparent at least at some points and which is permanently connected to the fastening means.
Figure 3:
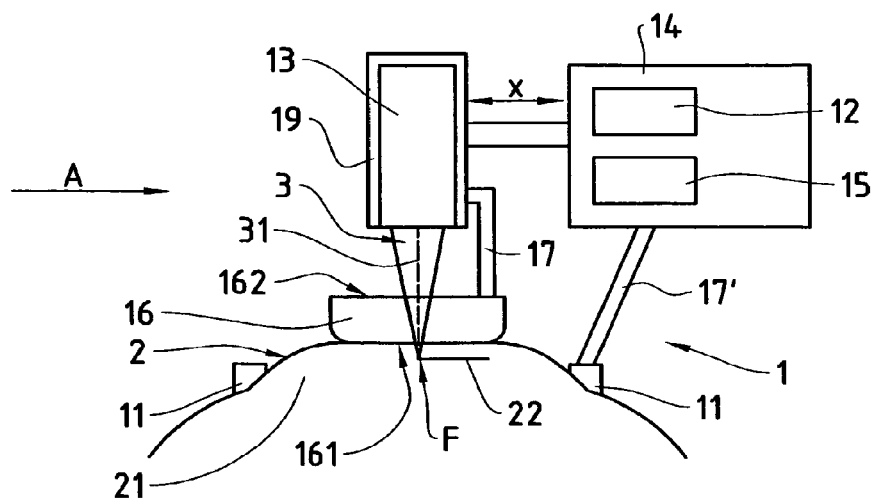
FIG. 3 shows a block diagram which schematically illustrates a design of the ophthalmological apparatus having a contact body which can be mounted on the eye and is transparent at least at some points and which is permanently connected to the light projector.

As illustrated in FIGS. 1, 2 and 3, the ophthalmological apparatus 1 is designed as a unit which can be applied manually and be fixed at the eye 2, and which comprises the light source 12 and the light projector 13 optically connected to the light source 12. Light source 12 comprises, for example, an appropriately wound femtosecond fibre laser.

Figure 6A:
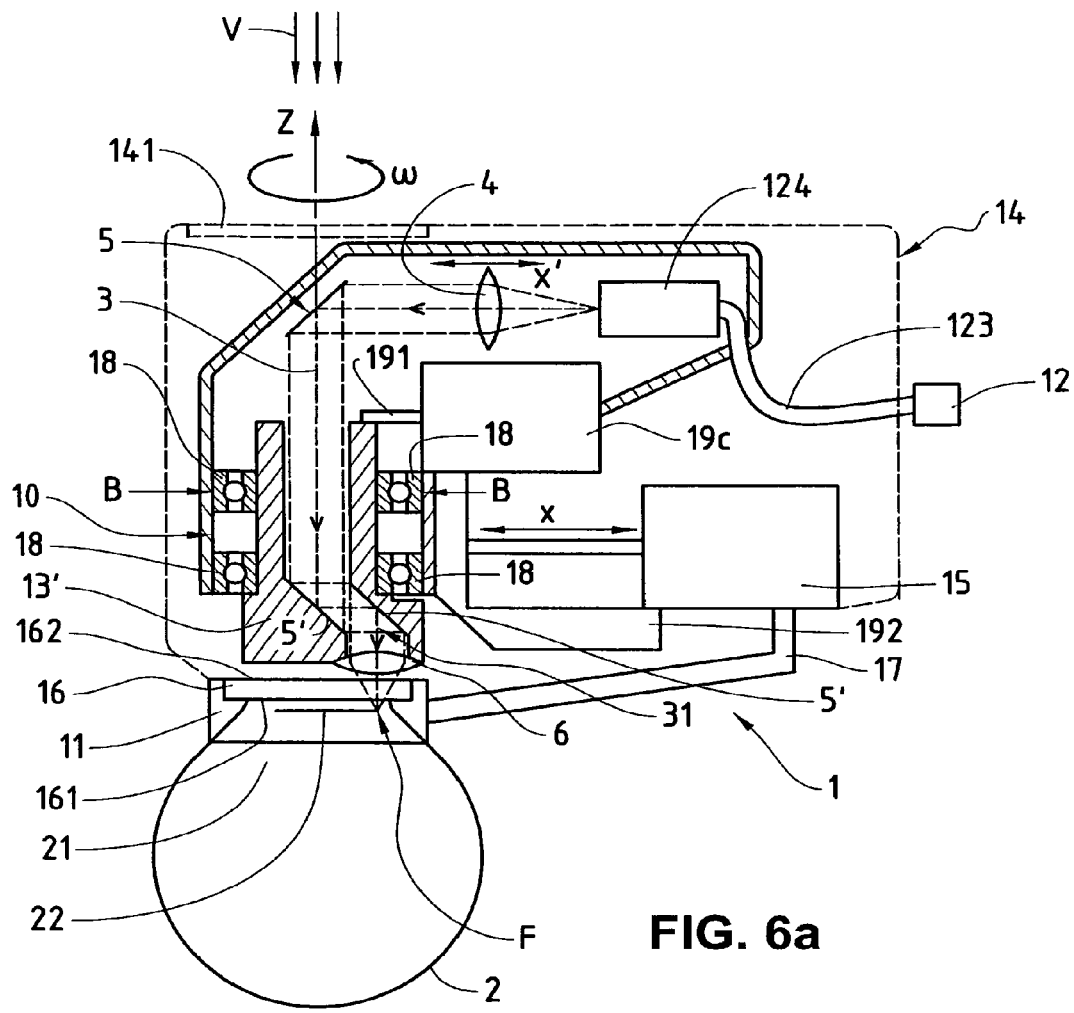
FIG. 6a shows a schematic cross section of a design of the ophthalmological apparatus with a first movement drive for translating the light projector along an axis of translation, and with a second movement driver for rotating the light projector about an axis of rotation.
Figure 7:
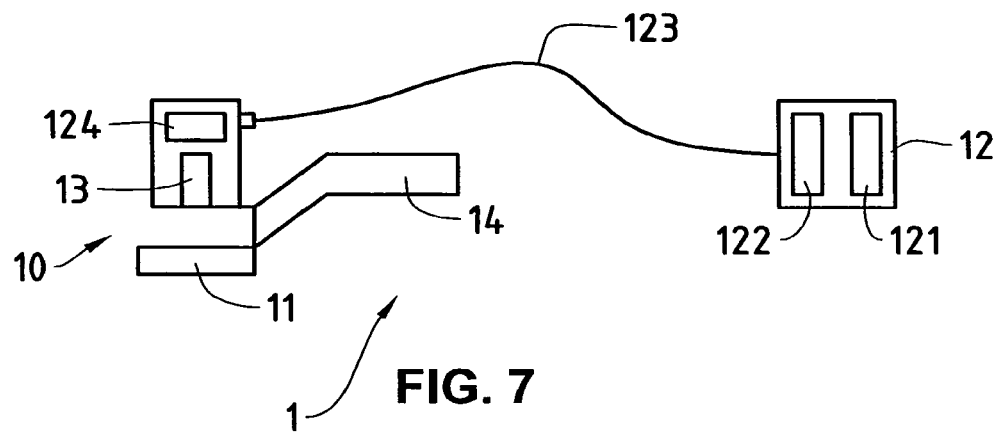
FIG. 7 shows a block diagram which schematically illustrates a design of the ophthalmological apparatus which comprises a handle and a light source which are interconnected via an optical transport line.

As illustrated in FIG. 7, in an alternative variant design the ophthalmological apparatus 1 comprises a hand-held appliance 10 which can be applied manually and be fixed at the eye 2, and which comprises a light projector 13 as well as a light source 12 which is external to the hand-held appliance 10 and is connected to the light projector 13 via an optical transport line 123. An appropriately designed ophthalmological apparatus 1 with such a hand-held appliance 10 is also illustrated schematically in FIG. 6a. As illustrated schematically in FIG. 7, the light source 12 comprises, for example, an optical oscillator 121 which is connected to the light projector 13 via an optical expander 122, via the optical transport line 123 and via an optical compressor 124, the optical transport line 123 comprising an optical amplifier. Alternatively, high power can be transmitted into the hand-held appliance 10 by using photonic crystals. The expander 122, amplifier and also the compressor 124 can then be situated externally relative to the hand-held appliance 10.

Figure 8:
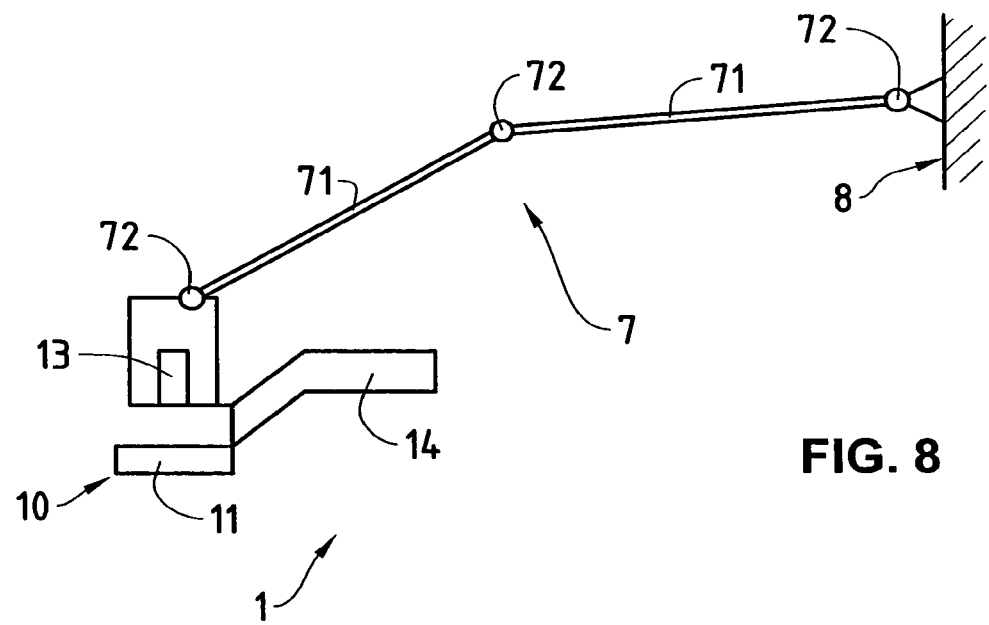
FIG. 8 shows a block diagram which schematically illustrates a design of the ophthalmological apparatus which comprises carrying means for fastening the ophthalmological apparatus movably on an object external to the ophthalmological apparatus.

As illustrated in FIG. 8, in a variant design the ophthalmological apparatus 1 can also be designed as a hand-held appliance 10 which can be manually applied and fixed at the eye 2, and which is provided with carrying means 7 in order to fasten the ophthalmological apparatus 1 or the hand-held appliance 10 movably on an object 8 which is external in relation to the ophthalmological apparatus 1 or the hand-held appliance 10. The carrying means 7 comprise, for example, a number of carrying elements 71 which are movably interconnected via joints 72 and can absorb the weight forces.

As illustrated in FIGS. 2, 3, 5a to 5c, and 6a, the ophthalmological apparatus 1 comprises a contact body 16 which can be mounted on the eye 2 and is transparent at least at some points. The contact body 16 preferably consists of transparent material, for example plastic, with a refractive index corresponding to the eye tissue 21. The area of the eye 2 which is contacted in the mounted state by the contact body 16, is denoted as contact area 161. The contact body 16 has a surface 162 averted from the contact area 161. The contact body 16 is preferably configured as a plane-parallel applanation body, and the surface 162 is equidistant from the contact area 161 (see FIGS. 2, 3, 5b, 5c and 6a). However, the contact body 16 can also be configured as a contour body which deforms the contacted area of the eye 2, for example in concave or convex fashion (see FIG. 5a). Both the applanation body and the contact body 16 configured as contour body can be designed such that the surface 162 is not equidistant from the contact area 161. In an alternative variant design, the contact body 16 can also have a cutout through which the laser pulses are projected.

The contact body 16 is preferably permanently connected to the fastening means 11, as illustrated in FIGS. 2 and 6a. In an alternative design, the contact body 16 is permanently connected to the light projector 13, as illustrated in FIG. 3.

The advantage thereby arises that the contact body 16 and the light projector 13 are precisely adjusted relative to one another.

As illustrated schematically in FIGS. 2, 3 and 6*a*, the ophthalmological apparatus 1 preferably comprises a holding apparatus 17 for removably holding the contact body 16. In particular, when the contact body 16 is permanently connected to the fastening means 11, as illustrated in FIGS. 2 and 6*a*, the holding apparatus 17 permits the removal of the contact body 16 and the fastening means 11 connected thereto, after the application of the ophthalmological apparatus 1 to the eye 2 of a patient. As illustrated in FIGS. 1 and 3, a corresponding holding device 17' can also be provided for removably holding the fastening means 11, if the latter are not permanently connected to the contact body 16. The removed contact body 16 and/or fastening means 11 can either be discarded or cleaned and sterilized. The holding device 17 or 17' can, for example, be configured such that the contact body 16 or the fastening means 11 are removably connected to the ophthalmological apparatus 1 by means of a screw lock or by means of a snap lock.

Both the simple variant design of the ophthalmological apparatus 1 without contact body 16, which is illustrated in FIG. 1, and the preferred variant design in which a contact body 16 is permanently connected to the fastening means 11, of which an example is illustrated in FIG. 2, and a further variant design, in which a contact body 16 is permanently connected to the light projector 13, of which an example is illustrated in FIG. 3, have a movement driver 15 and further movement means 19 in order to move the focal point F of the light pulses 3 projected by the light projector 13 such that it is possible to make tissue cuts 22 inside the eye tissue 21. The movement driver 15 is set up and arranged in order to move the light projector 13, and thus the focal point F, mechanically in a fashion equidistant from a movement surface.

FIGS. 4*a* to 4*f* respectively show a top view of the eye 2, the plane of the drawing preferably being parallel to the movement surface, from which the light projector 13 can be moved equidistantly. In a variant design, the light projector 13 can be moved equidistantly from a movement surface which is not flat. The combinations of translatory and/or rotatory movements, illustrated in FIGS. 4*a* to 4*f*, for the movement of the focal point F in the interior of the eye tissue 21 can be combined in each case with the abovementioned simple, with the abovementioned preferred and with the abovementioned further variant designs of the ophthalmological apparatus 1. In order to execute the combinations, illustrated in FIGS. 4*a* to 4*f*, of translatory and/or rotatory movements, the movement means 19 comprise a further movement driver 19*b*, 19*c* or movable light-deflecting optical elements 19*a*, as described below.

Figure 4A:
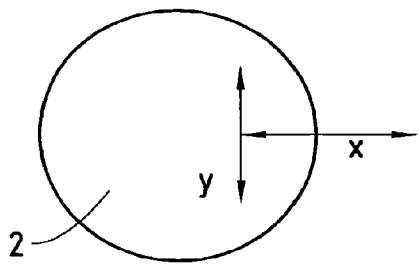
FIG. 4a shows, with reference to an eye, the combination of two translatory movements for moving the focal point of the light projector for the purpose of punctiform tissue breakdown in the interior of the eye tissue.

The combination of two translatory movements for moving the focal point F, which corresponds to a scanning operation, is illustrated in FIG. 4*a*. At least one of the translations is effected by a movement driver 15 which moves the light projector 13 mechanically, for example in the x-direction. Appropriate designs with a movement driver 15 for a translation of the light projector 13 in the x-direction are illustrated in FIGS. 2, 3 and 6*a*. The second translation is effected either by a further movement driver 19*b* (see FIG. 5*b*) which moves the light projector 13 mechanically in the y-direction, or by movable light-deflecting optical elements 19*a* (see FIG. 5*a*) which project the light pulses 3 along a scanning line in order to execute the tissue cut 22 in a y-direction. Movable optical elements 19*a* can be implemented, for example, as polygonal mirrors or galvanoscanners. In a variant design, translatory movements of the focal point F in the x-direction and in the y-direction are additionally superimposed by a fine movement of the focal point F, for example by means of optical microscans.

Figure 4B:
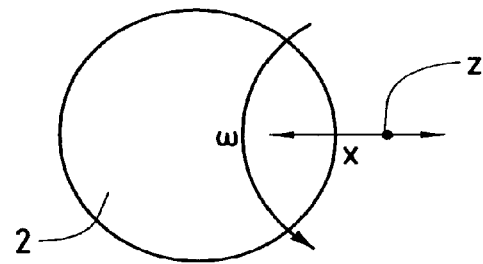
FIGS. 4b to 4e show, with reference to an eye, various combinations of a translatory and a rotatory movement for moving the focal point of the light projector for the purpose of punctiform tissue breakdown in the interior of the eye tissue.

FIG. 4*b* illustrates a combination of a translatory movement and a rotary movement for moving the focal point F, which resembles a milling operation, although only one cut is made in the interior of the eye tissue 21. The rotation is effected either by movable light-deflecting optical elements which project the light pulses 3 along the rotation arrow ω, or by a movement driver 19*c* (see FIG. 5*c* or 6*a*) which rotate the light projector 13 about the axis of rotation z, that is to say a rotation driver. The translation is effected by a movement driver 15 which moves the axis of rotation z mechanically in the x-direction (see FIG. 6*a*, in particular).

Figure 4C:
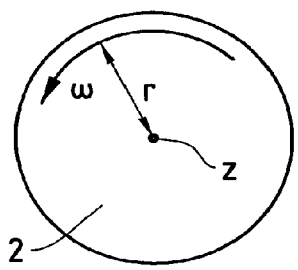

FIG. 4*c* illustrates a further combination of a translatory movement and a rotatory movement for moving the focal point F, which corresponds to a spiral movement as in the case of a record or a compact disc, or else can be designed in the form of concentric circles. The rotation is effected by movable light-deflecting optical elements which project the light pulses 3 along the rotation arrow ω. The translation is effected by means of a movement driver 15 which executes a radial translation of the light projector 13 on the radius r emanating from the axis of rotation z.

Figure 4D:
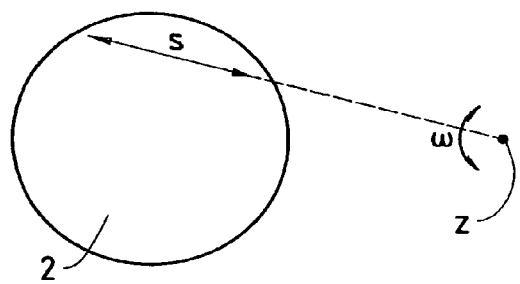

Illustrated in FIG. 4*d* is a further combination of a translatory movement and a rotatory movement for moving the focal point F, which corresponds the movement of a windscreen wiper of an automobile. The rotation is effected by a movement driver which pivots the light projector 13 to and fro about the axis of rotation z in accordance with the rotation arrow ω. The translation is effected by movable light-deflecting optical elements which project the light pulses 3 along a scanning line s running through the axis of rotation z.

Figure 4E:
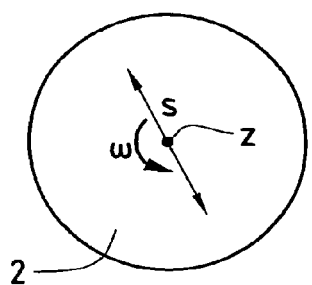

FIG. 4*e* illustrates a further combination of a translatory movement and a rotatory movement for moving the focal point F. The rotation is effected by a movement driver 19*c* (see FIG. 5*c* or 6*a*) which rotates the light projector 13 about the axis of rotation z, that is to say a rotation driver. The translation is effected by movable light-deflecting optical elements which project the light pulses 3 along a scanning line s running through the axis of rotation z.

Figure 4F:
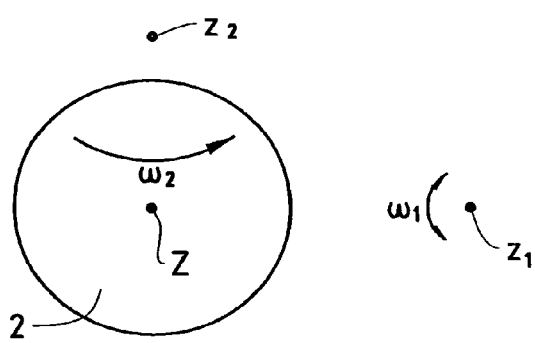
FIG. 4f shows, with reference to an eye, the combination of two rotatory movements for moving the focal point of the light projector for the purpose of punctiform tissue breakdown in the interior of the eye tissue.

FIG. 4*f* illustrates the combination of two rotatory movements for moving the focal point F. A first movement driver pivots the light projector 13 to and fro about the axis of rotation $z_1$ in accordance with the rotation arrow $w_1$. The second rotation is effected either by a second movement driver, which rotates the light projector 13 about the axis of rotation $z_2$ in accordance with the rotation arrow $w_2$, or by movable light-deflecting optical elements which project the light pulses 3 along the rotation arrow $w_2$. The axis of rotation $z_1$ can also run through the centre Z.

It should be remarked here concerning the above-described combinations of translatory and/or rotatory movements that the movements, executed by the movable light-deflecting optical elements, of the focal point F are executed much more quickly (oscillation frequencies of higher than 100 Hz are easy to implement technically) than the movements of the focal point F effected by mechanical movement drivers. Quick mechanical scanning movements can be produced only by rotations, since there is no need there to overcome inertia forces of oscillating masses. By combining quick movements along a scanning line and slow translation movements perpendicular to the scanning line, it is possible to produce cut surfaces just as quickly as is quick scanning also possible in the direction perpendicular to the scanning line. It is thus advantageously possible to reduce the outlay on equipment (that is to say elimination of a quick optical scanning axis) by suitably restricting the flexibility, that is to say by limiting the possible scanning patterns. Moreover, the limitation of flexibility can be used to reduce the overall size of the ophthalmological apparatus 1.

As illustrated in FIG. 2, in the preferred variant design of the ophthalmological apparatus 1, the movement driver 15 is designed and arranged such that the light projector 13 is displaced in the x-direction, which runs in the plane of the drawing. The light projector 13 is displaced in the x-direction in a fashion equidistant from the movement surface by means of the movement driver 15, in particular along a translation line or axis of translation. In FIG. 2, the movement surface contains the x-axis, for example, and is perpendicular to the plane of the drawing. The contact body 16 is preferably arranged such that the contact area 161 is equidistant from the movement surface. Consequently, with the focal length of the light projector 13 unchanged, that is to say with an unchanged distance from the light projector 13 to the focal point F, a tissue cut 22 is made in the interior of the eye tissue 21 in the x-direction in a fashion equidistant from the movement surface. The same also holds for the further variant design, illustrated in FIG. 3, of the ophthalmological apparatus 1 in which, by contrast with the preferred variant design, the contact body 16 is permanently connected to the light projector 13. As may be seen from FIGS. 2 and 3, the movement driver 15 and the light projector 13 are coupled and dimensioned such that the light projector 13 can be moved into a position in which at least a portion of the eye 2 can be examined by the user in top view upon fixing the ophthalmological apparatus 1 at the eye 2 (with light source 12 deactivated). The ophthalmological apparatus 1 can thereby be applied easily and accurately, for example like a conventional microkeratome. The process can be carried out as usual by the surgical microscope.

As illustrated schematically in FIGS. 2 and 3, the ophthalmological apparatus 1 comprises further movement means 19 for moving the focal point F in the y-direction perpendicular to the x-direction.

Figure 5A:
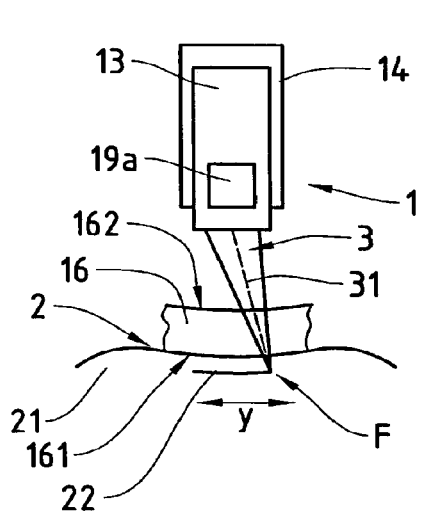
FIG. 5a shows a block diagram which schematically illustrates a design of the ophthalmological apparatus with light-deflecting optical elements for the purpose of displacing the focal point along a scanning line, in a side view.
Figure 5B:
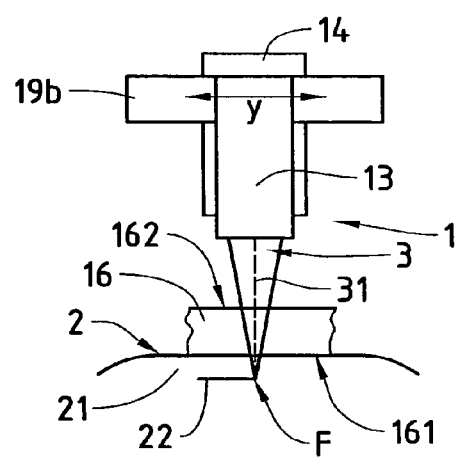
FIG. 5b shows a block diagram which schematically illustrates a design of the ophthalmological apparatus with a movement driver for translating the light projector along an axis of translation, in a side view.
Figure 5C:
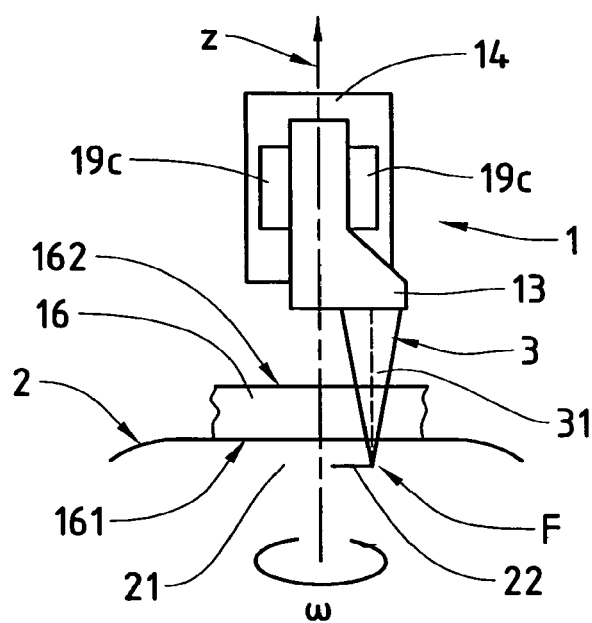
FIG. 5c shows a block diagram which schematically illustrates a design of the ophthalmological apparatus with a movement driver for rotating the light projector about an axis of rotation, in side view.

FIGS. 5*a*, 5*b* and 5*c* illustrate various designs, which can be combined with the variant designs illustrated in FIGS. 2 and 3, of the ophthalmological apparatus 1 with movement means 19 for moving the focal point F in the y-direction perpendicular to the x-direction. FIGS. 5*a*, 5*b* and 5*c* show schematically a view of a detail of the ophthalmological apparatus 1 in the direction shown in FIGS. 2 and 3 by the arrow A.

In the variant design in accordance with FIG. 5*a*, the ophthalmological apparatus 1 comprises movable light-deflecting optical elements 19*a* which, for the purpose of making the tissue cut 22 in the y-direction, project the light pulses 3 onto a scanning line which runs in a equidistant fashion from a concave or convex movement surface. The contact body 16 is preferably of concave or convex design and arranged such that the contact area 161 is equidistant from the concave or convex movement surface. As a result, with an unchanged focal length of the light projector 13, a tissue cut 22 is made in the interior of the eye tissue 21 in a fashion equidistant from the concave or convex movement surface. The movable light-deflecting optical elements 19*a* permit quick and repeated scanning in the y-direction (for example at a frequency of from 100 to 1000 Hz). Examples of light-deflecting optical elements 19*a* comprise, for instance, polygon scanners, galvanoscanners, tilting mirrors (driven by piezo-actuators), microoptoelectromechanical systems (MicroOptoElectroMechanical Systems, MOEMS), acoustooptical modulators (AOM) or microlens array scanners which are controlled, for example, by appropriately programmed control means. The integration of anamorphotic optics (for example cylindrical lens) along the scanning line permits high numerical apertures transverse to the scanning direction.

In the variant design in accordance with FIG. 5*b*, the ophthalmological apparatus 1 comprises a further movement driver 19*b* which is arranged such that the light projector 13 is displaced mechanically along an axis of translation in the y-direction in a fashion equidistant from a flat movement surface. The contact body 16 is arranged, in turn, such that the contact area 161 is equidistant from the movement surface. As a result, with an unchanged focal length of the light projector 13 a tissue cut 22 is made in the y-direction in the interior of the eye tissue 21 in a fashion equidistant from the flat movement surface.

In the variant design in accordance with FIG. 5*c*, the ophthalmological apparatus 1 comprises a further movement driver 19*c*, which is designed and arranged such that the light projector 13 is rotated in accordance with the rotation arrow ω about one or two axis/axes of rotation z normal to a flat movement surface. The contact body 16 is arranged, in turn, such that the contact area 161 is equidistant from the movement surface. As a result, with an unchanged focal length of the light projector 13 a circular tissue cut 22 is made in the interior of the eye tissue 21 in a fashion equidistant from the flat movement surface.

In order to move the focal point F in the z-direction, which is perpendicular to the x- and y-directions and shown in FIGS. 5*c* and 6*a*, the ophthalmological apparatus 1 is set up to control the spacing between the focal point F and the movement surface. In a variant design, the movement means 19 comprise a further movement driver (not illustrated), which moves the light projector 13 in the z-direction in order to vary the spacing between the focal point F and the movement surface. However, the ophthalmological apparatus 1 is preferably set up to control the position of the focal point F along the axis of projection 31 of the light pulses 3, that is to say to vary the position of the focal point F by means of optical elements. The focal length of the light projector 13 can be varied, for example, by moving the lens 4 in the x'-direction, as shown in FIG. 6*a*. By moving the focal point F in the z-direction, it is possible to make tissue cuts in the interior of the eye tissue 21 in the z-direction, vertical to the movement surface.

Figure 6B:
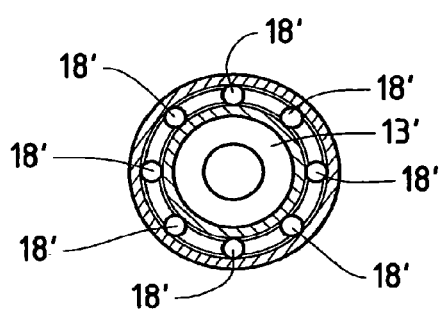
FIG. 6b shows a cross section which schematically illustrates a design of the bearing of the light projector for rotating the light projector.

FIG. 6*a* shows a schematic cross section of a design of the ophthalmological apparatus 1 in the state mounted on the eye 2. The design shown in FIG. 6*a* of the ophthalmological apparatus 1 corresponds to a combination of the variant designs shown in FIGS. 2 and 5*c*, and permits movements of the focal point F in accordance with FIG. 4*b*. The design shown in FIG. 6*a* of the ophthalmological apparatus 1 comprises a hand-held appliance 10 with a light projector which is connected via an optical transport line 123 to a light source 12 external to the hand-held appliance 10. In accordance with the design illustrated in FIG. 6*a*, the light projector comprises the hollow body 13', the mirrors 5' and lens 6, attached to the hollow body 13', as well as the lens 4 and the mirror 5. Light pulses 3 generated in the light source 12 are focussed at the focal point F via the lens 4, the mirrors 5 and 5' and via the lens 6, and projected into the interior of the eye tissue 21. The hollow body 13' is mounted by means of the bearing 18 such that it can rotate about the axis of rotation z. FIG. 6*b* shows a cross section through the bearing 18 and the hollow body 13' of the light projector at the point shown in FIG. 6*a* by the arrow B, the arrangement of ball bearings 18' being purely schematic. It will be understood by the person skilled in the art that other types of bearing are possible. The hollow body 13' of the light projector is rotated about the axis of rotation z in a fashion driven by the movement driver 19c via the drive element 191. The mirror 5 is rigidly connected to the movement driver 19c and reflects incoming light pulses 3 onto the mirrors 5', which are permanently connected to the rotatable hollow body 13' of the light projector and move about the axis of rotation z with the hollow body 13'. The hollow body 13' of the light projector, the bearings 18 and the movement driver 19c are attached to a carrier 192 which can be displaced mechanically along an axis of translation in the x-direction by the movement driver 15. As indicated in FIG. 6a, the ophthalmological apparatus 1 comprises a housing (illustrated by dashes) which serves as a handle 14 and is configured to enable to translation movement in the x-direction and the rotation about the axis of rotation z. The housing configured as a handle 14 has a cutout 141 which permits an unimpeded view of the eye 2 from the direction indicated by the arrows V. It may be seen from FIG. 6a how it is possible by combining the mechanical scanning movements and small projection optics to implement a compact ophthalmological apparatus 1 which nevertheless has a very high numerical aperture (the design in accordance with FIG. 6a has approximately a numerical aperture of 0.5).

Figure 9A:
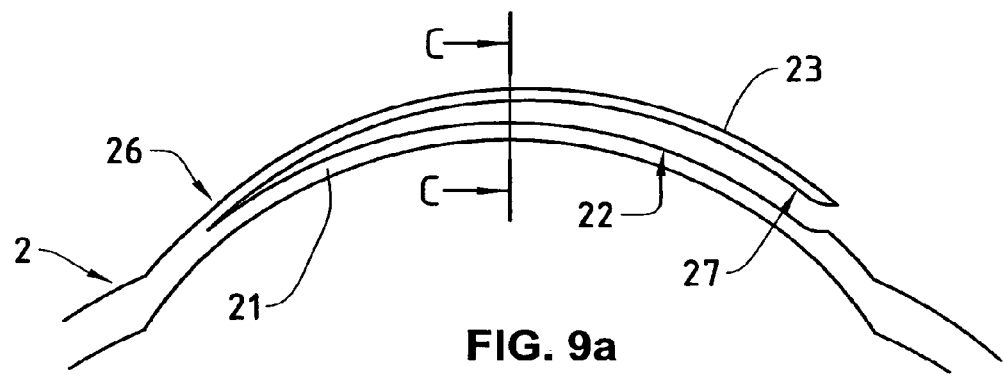
FIG. 9a shows a cross section of a tissue flap which, separated from eye tissue, remains connected to the eye in a residual area.
Figure 9B:
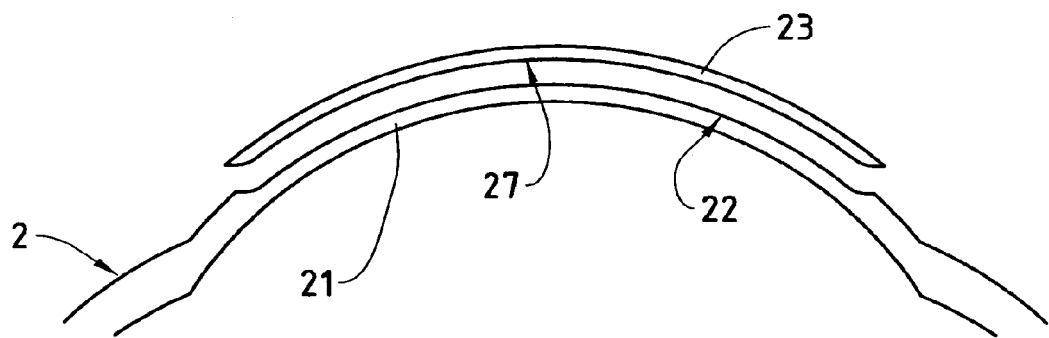
Figure 10A:
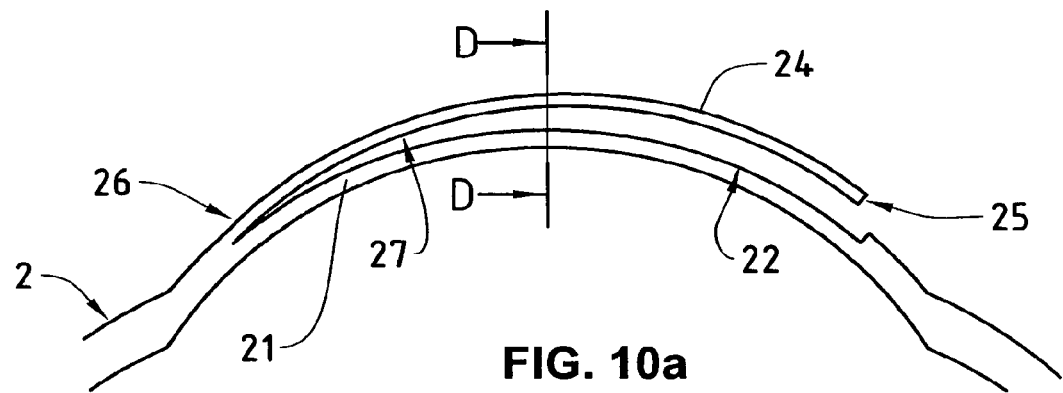
FIG. 10a shows a cross section of a tissue piece which, separated from eye tissue, remains connected to the eye in a residual area, and which has lateral surfaces.
Figure 10B:
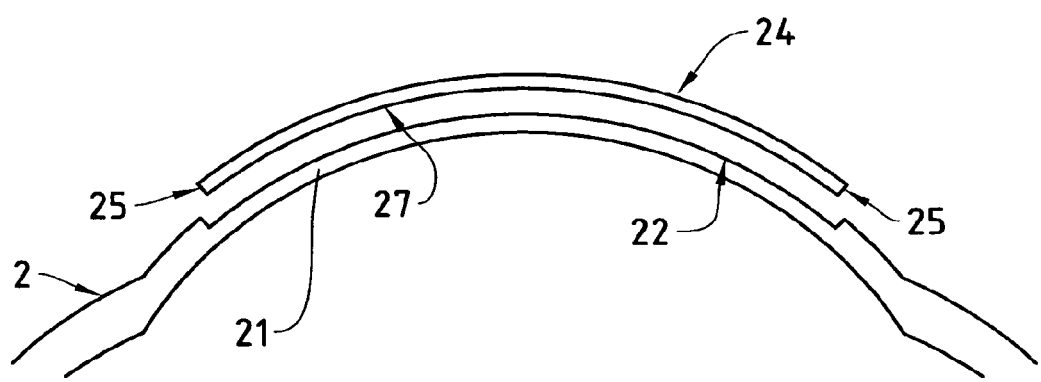
FIG. 10b shows a further cross section of the tissue piece illustrated in FIG. 10a with lateral surfaces.

FIGS. 9a, 9b, 10a and 10b show examples of tissue pieces which are separated from the remaining eye tissue 21 by the ophthalmological apparatus 1 by means of focussed projection of light pulses onto focal points F in the interior of the eye tissue 21 and by the punctiform tissue breakdown effected thereby. The tissue flap 23 illustrated in FIG. 9a is produced in the applanated state of the eye 2 by a flat tissue cut 22 in the interior of the eye tissue 21, and remains connected to the eye 2 in a residual area 26. FIG. 9b shows a cross section through the tissue flap 23 at the point which is indicated in FIG. 9a by the arrows C. The tissue piece 24 shown in FIG. 10a is also produced in the applanated state of the eye 2 by a flat tissue cut 22 in the interior of the eye tissue 21. The tissue piece 24 likewise remains connected to the eye 2 in a residual area 26, and has lateral surfaces 25 which are produced by vertical cuts. FIG. 10b shows a cross section through the tissue piece 24 with the lateral surfaces 25 at the point indicated in FIG. 10a by the arrows D. Other edge shapes are possible at the location of the lateral surfaces 25 when, for example, lens 4 in FIG. 6a is displaced vertically in addition. The base surfaces 27 of the tissue flap 23 illustrated in FIG. 9a and of the tissue piece 24 shown in FIG. 10a are produced by the flat tissue cut 22, that is to say by moving the focal point F in a fashion equidistant from the movement surface. In order to limit the action range within which the focal point F can be moved, the movement driver 15 and the movement means 19, in particular 19a, 19b and 19c, are limited mechanically and/or by programmable control means in their movement range. Particularly for the movement of the focal point F in a fashion equidistant from the movement surface, the movement driver 15 and the movement means 19, in particular 19a, 19b and 19c, are preferably guided mechanically. Movement surfaces of great precision can thereby be realized by mechanical guides. Precise movement surfaces can easily be implemented by mechanical guides particularly in the case of a constant working distance of the light projector 13. Programmable control means are suitable, in particular, for the configuration of individually dimensioned tissue cuts 22 and/or of tissue cuts for separating tissue pieces 24 which cannot just be made by simple flat tissue cuts 22. The programmable control means comprise, for example, a processor and a memory in which there are stored programmes and cut parameters, or non-programmable electronic circuits which comprise memories for storing cut parameters.

During application of the ophthalmological apparatus 1, the light projector 13 is preferably firstly displaced by means of the movement driver 15 such that at least a portion of the eye 2 can be freely examined in top view. Thereafter, the ophthalmological apparatus 1 is mounted on the eye 2 in the desired area and fixed at the eye 2 with the aid of the fastening means 11. If appropriate, the contact body 16 has reference marks for accurate positioning of the ophthalmological apparatus 1 on the eye. The ophthalmological apparatus 1 is then activated, and the focal point F is moved automatically by the movement driver 15 and the movement means 19, in particular 19a, 19b and 19c, preferably under mechanical guidance and limitation and/or under programmed control.

The invention claimed is:

1. An ophthalmological apparatus, comprising: a light source, and an appliance for manual application onto an eye of a patient, the appliance comprising:
   fastening means configured to fix the appliance on the eye of the patient,
   a light projector, optically connected to the light source, for a focused projection of light pulses for punctiform tissue breakdown at a focal point in the interior of the eye tissue of the eye of the patient, and having a projection axis, and
   a movement driver configured to mechanically move the light projector and its projection axis, relative to the eye of the patient, with the appliance being fixed on the eye of the patient, to move the focal point of the punctiform tissue breakdown and thereby produce cuts in the eye of the patient by moving said focal point~
   wherein the movement driver and the light projector are set up and coupled such that the light projector can be moved equidistantly from a movement surface.

2. The ophthalmological apparatus according to claim 1, wherein the movement driver and the light projector are set up and coupled such that the light projector is movable into a position in which at least a portion of the eye can be examined in top view upon fixing the appliance on the eye.

3. The ophthalmological apparatus according to claim 1, wherein the movement driver is set up to move the light projector along a translation line equidistant from the movement surface.

4. The ophthalmological apparatus according to claim 1, wherein the movement driver is set up to move the light projector about an axis of rotation normal to the movement surface.

5. The ophthalmological apparatus according to claim 1, wherein the movement driver is set up to move the light projector along a translation line equidistant from the movement surface, and in that the appliance comprises a further movement driver, which is set up to move the light projector about an axis of rotation normal to the movement surface.

6. The ophthalmological apparatus according to claim 1, wherein the ophthalmological apparatus is set up to control the spacing between the focal point and the movement surface.

7. The ophthalmological apparatus according to claim 1, wherein the ophthalmological apparatus is set up to control the position of the focal point along the axis of projection of the light pulses.

8. The ophthalmological apparatus according to claim 1, wherein the light projector comprises light-deflecting optical elements for the focussed projection of the light pulses along a scanning line.

9. The ophthalmological apparatus according to claim 1, wherein the ophthalmological apparatus comprises a contact body which can be mounted onto the eye and is transparent at least at some points and is designed and arranged such that it places equidistantly from the movement surface an area of the eye which is contacted in the mounted state.

10. The ophthalmological apparatus according to claim 9, wherein the contact body is of plane-parallel configuration.

11. The ophthalmological apparatus according to claim 9, wherein the contact body is permanently connected to the fastening means.

12. The ophthalmological apparatus according to claim 9, wherein the contact body is permanently connected to the light projector.

13. The ophthalmological apparatus according to claim 9, wherein the ophthalmological apparatus comprises a holding apparatus for removably holding the contact body.

14. The ophthalmological apparatus according to claim 1, wherein the movement driver and the light projector are set up and coupled such that the light projector can be moved equidistantly from a flat movement surface.

15. The ophthalmological apparatus according to claim 1, wherein the light source comprises a femtosecond laser.

16. The ophthalmological apparatus according to claim 15, wherein the femtosecond laser is designed as a fibre laser.

17. The ophthalmological apparatus according to claim 1, wherein the light source is connected to the light projector via an optical transport line which is designed as a photonic crystal.

18. The ophthalmological apparatus according to claim 1, wherein the light source comprises an optical oscillator, and in that the optical oscillator is connected to the light projector via an optical expander, via an optical transport line and via an optical compressor, the optical transport line comprising an optical amplifier.

19. The ophthalmological apparatus according to claim 18, wherein the optical transport line is designed as a photonic crystal.

20. The ophthalmological apparatus according to claim 1, wherein the fastening means are set up to fix the appliance by low pressure to the eye.

21. The ophthalmological apparatus according to claim 1, wherein the ophthalmological apparatus further comprises control means for controlling the position of the focal point in such a way that the tissue breakdown in the interior of the eye tissue separates from the remaining eye tissue a tissue piece which remains connected to the eye in a residual area, the tissue piece having lateral surfaces which are produced by varying the spacing of the focal point from the movement surface.

22. The ophthalmological apparatus according to claim 1, wherein the ophthalmological apparatus is designed as a unit, which unit can be applied manually and can be fixed to the eye, and which unit comprises the light source and the light projector optically connected to the light source.

23. An ophthalmological apparatus comprising—
a light source, and
an appliance for manual application onto an eye of a patient, the appliance comprising:
fastening means configured to fix the appliance on the eye of the patient,
a light projector, optically connected to the light source, for a focused projection of light pulses for punctiform tissue breakdown at a focal point in the interior of the eye tissue of the eye of the patient, and having a projection axis, and
a movement driver configured to mechanically move the light projector and its projection axis, relative to the eye of the patient, with the appliance being fixed on the eye of the patient, to move the focal point of the punctiform tissue breakdown and thereby produce cuts in the eye of the patient by moving said focal point,
wherein the ophthalmological apparatus further comprises carrying means for fastening the appliance movably on an object external to the appliance.

24. The ophthalmological apparatus according to claim 1, wherein the ophthalmological apparatus is set up to move the focal point such that the tissue breakdown in the interior of the eye tissue separates from the remaining eye tissue a tissue flap which remains connected to the eye in a residual area.

* * * * *